(12) United States Patent
Bedford et al.

(10) Patent No.: US 8,783,019 B2
(45) Date of Patent: Jul. 22, 2014

(54) APPARATUS AND METHOD FOR ONBOARD PERFORMANCE MONITORING OF OXIDATION CATALYST

(75) Inventors: Joshua Clifford Bedford, Farmington Hills, MI (US); Julian C. Tan, Vernon Hills, IL (US); Janean E Kowalkowski, Northville, MI (US)

(73) Assignee: GM Global Technology Operations LLC, Detroit, MI (US)

( * ) Notice: Subject to any disclaimer, the term of this patent is extended or adjusted under 35 U.S.C. 154(b) by 149 days.

(21) Appl. No.: 13/604,046

(22) Filed: Sep. 5, 2012

(65) Prior Publication Data
US 2014/0060007 A1 Mar. 6, 2014

(51) Int. Cl.
*F01N 3/00* (2006.01)
*F01N 3/20* (2006.01)
*G01N 27/41* (2006.01)
*G01N 27/411* (2006.01)
*G01N 33/00* (2006.01)

(52) U.S. Cl.
CPC .............. *F01N 3/206* (2013.01); *F01N 3/2066* (2013.01); *F01N 2560/026* (2013.01); *F01N 2610/02* (2013.01); *G01N 27/41* (2013.01); *G01N 27/4114* (2013.01); *G01N 33/0037* (2013.01)
USPC ................... 60/286; 60/274; 60/276; 60/279; 60/301; 204/424; 204/425; 204/427; 204/432

(58) Field of Classification Search
CPC ..................... F01N 2610/02; F01N 2900/1614
USPC ................... 60/274, 276, 286, 297, 301, 303; 204/424, 425, 426, 427, 432
See application file for complete search history.

(56) References Cited

U.S. PATENT DOCUMENTS

| | | | | |
|---|---|---|---|---|
| 5,034,112 | A * | 7/1991 | Murase et al. | 204/406 |
| 6,076,393 | A * | 6/2000 | Kato et al. | 73/31.05 |
| 6,303,011 | B1 * | 10/2001 | Gao et al. | 204/425 |
| 6,701,707 | B1 | 3/2004 | Upadhyay et al. | |
| 6,775,623 | B2 | 8/2004 | Ali et al. | |
| 6,899,093 | B2 | 5/2005 | Center | |
| 7,114,325 | B2 * | 10/2006 | Surnilla et al. | 60/276 |
| 7,134,273 | B2 | 11/2006 | Mazur et al. | |
| 7,644,576 | B2 * | 1/2010 | Inagaki et al. | 60/276 |
| 8,359,841 | B2 * | 1/2013 | Goya et al. | 60/295 |
| 2009/0223207 | A1 | 9/2009 | Ren | |
| 2010/0077833 | A1 | 4/2010 | Wang et al. | |
| 2010/0161242 | A1 | 6/2010 | Wang et al. | |

* cited by examiner

*Primary Examiner* — Binh Q Tran
(74) *Attorney, Agent, or Firm* — Cantor Colburn LLP

(57) ABSTRACT

An exhaust treatment system is disclosed that can diagnose the performance of an exhaust treatment oxidation catalyst in converting NO to $NO_2$. The exhaust treatment system is fluidly coupled to an internal combustion engine, and includes an oxidation catalyst disposed in an engine exhaust stream; a reductant source for injecting a reductant into the exhaust stream downstream of the oxidation catalyst; an SCR catalyst disposed in the exhaust stream downstream of the reductant source; and a gas sensor, disposed in the exhaust stream downstream of the oxidation catalyst and upstream of the reductant source, comprising a plurality of sensing or pumping cells that measures NO concentration in the exhaust gas and $NO_2$ concentration in the exhaust gas.

15 Claims, 1 Drawing Sheet

US 8,783,019 B2

APPARATUS AND METHOD FOR ONBOARD PERFORMANCE MONITORING OF OXIDATION CATALYST

FIELD OF THE INVENTION

Exemplary embodiments of the present invention are related to monitoring engine exhaust systems and, more specifically, to an apparatus and method for determining the NO to $NO_2$ conversion effectiveness of an oxidation catalyst (DOC) in the engine exhaust stream.

BACKGROUND

Significant interest has been focused on the reduction of certain constituents in internal combustion engine exhaust. Recently, focus has been placed on diesel engines. Diesel engine exhaust typically contains gaseous emissions such as carbon dioxide ("$CO_2$"), water vapor ("$H_2O$"), unburned hydrocarbons ("HC"), carbon monoxide ("CO"), and oxides of nitrogen ("$NO_x$") including NO and $NO_2$, along with solid and/or liquid condensed phase materials referred to as particulates. Treatment of diesel engine exhaust may involve various catalytic devices having one or more catalysts disposed on a substrate for reducing the levels of regulated constituents in the diesel exhaust. For example, diesel exhaust treatment systems may include an oxidation catalyst, also known as a diesel oxidation catalyst ("DOC"), to convert HC and CO to $CO_2$ and water, a catalyst for the reduction of $NO_x$, and a particulate filter, also known as a diesel particulate filter ("DPF"), for removal of particulates.

One diesel exhaust treatment technology of particular interest is the use of a selective catalytic reduction ("SCR") catalyst for the reduction of $NO_x$. This technology involves the catalytically-enhanced reduction of NO to nitrogen and oxygen by ammonia or an ammonia source such as urea. The efficiency of this reduction reaction is significantly impacted by the ratio of $NO_2$:$NO_x$ in the exhaust stream entering the SCR reactor. The impact of this ratio on SCR efficiency is especially pronounced at lower operating temperatures (e.g., <300° C.). For a typical zeolite-based SCR catalyst, the desired $NO_2$:$NO_x$ ratio is about 0.5, which is required for a fast SCR reaction. Exhaust coming out of an engine, however, often exhibits a less than ideal $NO_2$:$NO_2$ ratio of less than 0.2. Fortunately, a DOC device, which is often placed upstream of an SCR reactor in diesel exhaust treatment systems, is capable of converting NO to $NO_2$ so that the ratio of $NO_2$:$NO_x$ in the exhaust stream entering the SCR reactor can more closely approach the desired ratio.

One issue, however, with reliance on a DOC device to convert NO to $NO_2$ in order to enhance the NO:$NO_2$ ratio in the exhaust stream entering the SCR device is that the NO to $NO_2$ conversion effectiveness of a DOC device can vary with aging and/or operating conditions. It would therefore be desirable to have the capability, on board of a vehicle, to monitor the NO to $NO_2$ conversion effectiveness of a DOC exhaust treatment device. Unfortunately, most $NO_x$ sensors are not capable of distinguishing between NO and $NO_2$, so direct on-board measurement of the DOC's NO to $NO_2$ conversion efficiency is not feasible. Accordingly, it is desirable to provide a system and method for measurement of a DOC exhaust treatment device's effectiveness of converting NO to $NO_2$.

SUMMARY OF THE INVENTION

In one exemplary embodiment of the invention, an exhaust treatment system fluidly coupled to an internal combustion engine comprises:

an oxidation catalyst disposed in an engine exhaust stream;

a reductant source for injecting a reductant into the exhaust stream downstream of the oxidation catalyst;

an SCR catalyst disposed in the exhaust stream downstream of the reductant source; and a gas sensor, disposed in the exhaust stream downstream of the oxidation catalyst and upstream of the reductant source, comprising a plurality of sensing or pumping cells, wherein a first cell is capable of producing a first output that is indicative of a concentration of $NO_2$ alone or in combination with one or more other constituents, and a second cell is capable of producing a second output that is indicative of a concentration of NO alone or in combination with one or more other constituents, and further wherein if the first output is indicative of the concentration of $NO_2$ in combination with one or more other constituents, the sensor comprises cells with sensing capabilities sufficient to isolate the contribution of $NO_2$ concentration to the first output, and if the second output is indicative of the concentration of NO in combination with one or more other constituents, the sensor comprises cells with sensing capabilities sufficient to isolate the contribution of NO concentration to the second output.

In another exemplary embodiment of the invention, there is a method of assessing performance an exhaust treatment system comprising an oxidation catalyst disposed in an engine exhaust stream, a reductant source for injecting a reductant into the exhaust stream downstream of the oxidation catalyst, and an SCR catalyst disposed in the exhaust stream downstream of the reductant source. The method comprises:

reading the output of a gas sensor, disposed in the exhaust stream downstream of the oxidation catalyst, to determine the concentrations of NO and $NO_2$ in the exhaust stream downstream of the oxidation catalyst, the gas sensor comprising a plurality of sensing or pumping cells, wherein a first cell is capable of producing a first output that is indicative of a concentration of $NO_2$ alone or in combination with one or more other constituents, and a second cell is capable of producing a second output that is indicative of a concentration of NO alone or in combination with one or more other constituents, and further wherein if the first output is indicative of the concentration of $NO_2$ in combination with one or more other constituents, the sensor comprises cells with sensing capabilities sufficient to isolate the contribution of $NO_2$ concentration to the first output, and if the second output is indicative of the concentration of NO in combination with one or more other constituents, the sensor comprises cells with sensing capabilities sufficient to isolate the contribution of NO concentration to the second output; and generating an alert signal if either or both of the concentrations of NO and $NO_2$ or the ratio of NO content to $NO_2$ content in the exhaust stream downstream of the oxidation catalyst fall outside a target level or range.

The above features and advantages and other features and advantages of the invention are readily apparent from the following detailed description of the invention when taken in connection with the accompanying drawings.

BRIEF DESCRIPTION OF THE DRAWINGS

Other objects, features, advantages and details appear, by way of example only, in the following detailed description of embodiments, the detailed description referring to the drawings in which.

DESCRIPTION OF THE EMBODIMENTS

Figure 1:
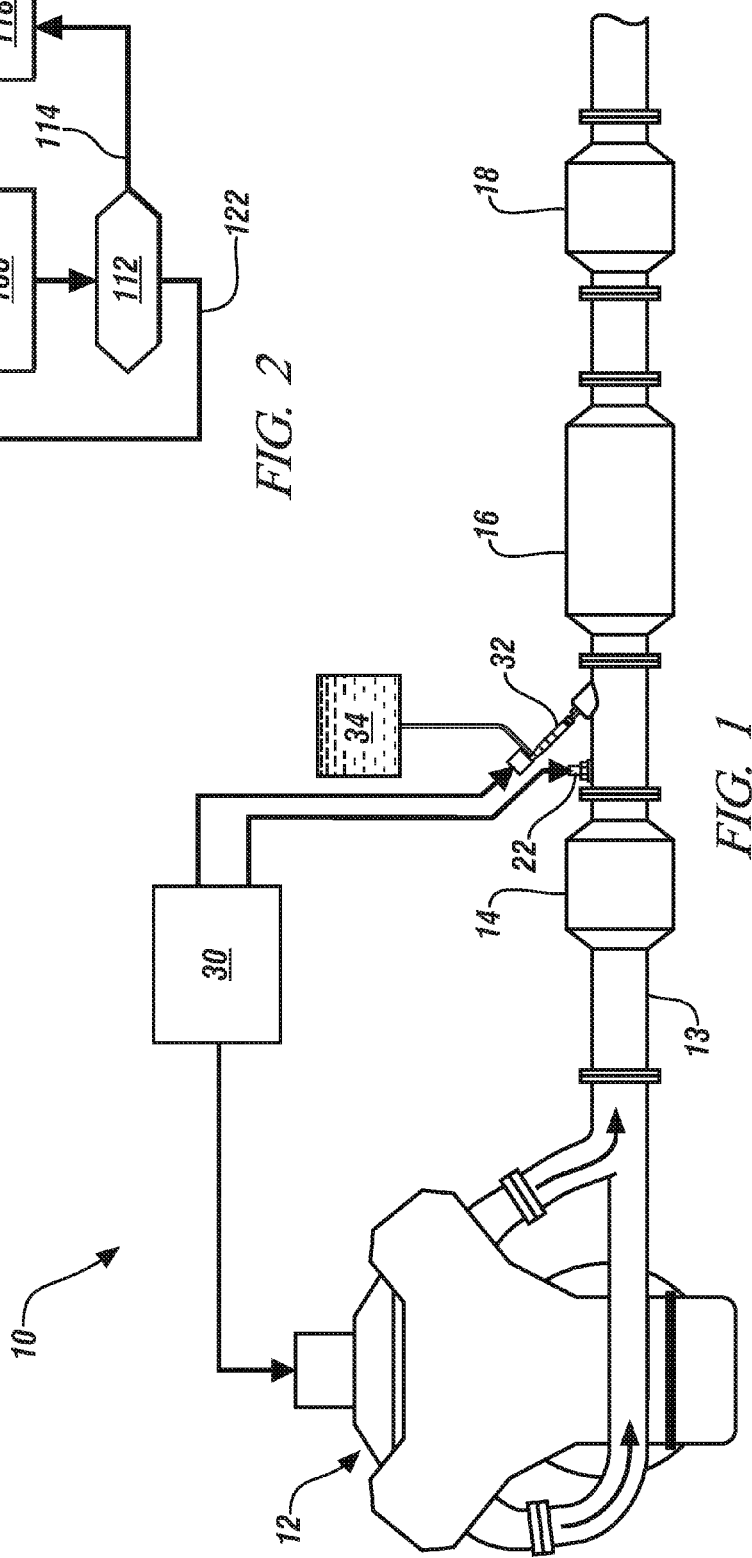
FIG. 1 is schematic view an exhaust treatment system according to an exemplary embodiment of the invention.

Referring now to FIG. 1, an exemplary embodiment of the invention is directed to an exhaust treatment system 10 for reduction of regulated components of engine exhaust from an internal combustion engine such as diesel engine 12. The system includes an exhaust conduit 13, which collects exhaust from the diesel engine 12 and transports it to the treatment devices in the system, such as oxidation catalyst 14, SCR catalyst 16, and particulate filter 18. Gas sensor 22 measures NO and $NO_2$ concentration values in the exhaust gas downstream of oxidation catalyst 14. Other sensors (not shown), such as temperature sensors, oxygen sensors, ammonia sensors, and the like may be incorporated at various positions in the exhaust treatment system as is known in the art.

Reductant source 34 is connected to reductant injector 32 for injecting reductant into the engine exhaust stream upstream of SCR catalyst 16 to enhance the effectiveness of the SCR catalyst at reducing $NO_x$ emissions. The reductant may include any known reducing agent, such as ammonia or urea. Urea is commonly used as a reducing agent used for motor vehicle exhaust SCR treatment schemes, and is also referred to as Diesel Exhaust Fluid (DEF) by the US EPA.

Control module 30 receives inputs from gas sensor 22 and optionally other sensor components and communicates output settings to reductant injector 32. Control module 30 also receives input data and communicates output settings to various components in engine 12, as well as other sensors and devices in other on-board vehicle systems. Control module 30 may be any known type of control module, such as a microprocessor coupled with a storage medium containing data and instructions for controlling system 10 and carrying out methods according to exemplary embodiments of the invention.

In accordance with exemplary embodiments of the invention, control module 30 diagnoses NO to $NO_2$ conversion effectiveness of the oxidation catalyst 14, which can in turn provide useful information regarding the efficiency of the SCR in reducing $NO_x$ emissions and can control engine operating parameters for effective exhaust warm-up and optimization of urea solution (DEF) dosing rate accordingly. In so doing, control module 30 relies on the relative amounts of NO and $NO_2$ in the exhaust gas downstream of the oxidation catalyst.

Figure 2:
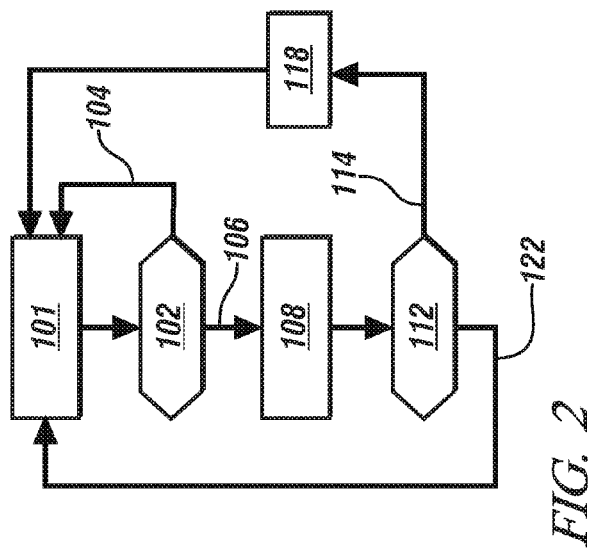
FIG. 2 is a block diagram representing a method of determining NO to $NO_2$ conversion effectiveness in an oxidation catalyst according to exemplary embodiments of the invention.

Turning now to FIG. 2, a flow chart illustrating portions of a control algorithm in accordance with an exemplary embodiment of the invention is illustrated for performing diagnostics to determine NO to $NO_2$ conversion effectiveness of an oxidation catalyst. In this exemplary embodiment, control algorithm 100 is implemented as the result of an electronic control module ("ECM") initiated diagnostic during operation of a vehicle, in which case the algorithm at step 101 checks whether conditions exist to cause initiation of the diagnostic routine to determine NO to $NO_2$ conversion effectiveness of the oxidation catalyst. Such conditions can vary depending on the particular design and operating parameters of the engine and its exhaust system and may include, for example, the passage of accumulated time of engine operation, suitable DOC inlet and/or outlet temperatures, anomalous sensor readings such as an unexpected concentration of ammonia in the exhaust stream downstream of the SCR catalyst, or other factors as would be recognized by one skilled in the art.

The algorithm logic path then moves to decision node 102 where the algorithm assesses whether conditions for proceeding with the diagnostic are satisfied. If the conditions are not satisfied, the logic path loops along path 104 back to box 101. If the conditions are satisfied, the logic path proceeds along path 106 to box 108, which provides for monitoring the NO and $NO_2$ levels in the exhaust gas downstream of the gas sensor 22 (FIG. 1). Thermal response profile of the oxidation catalyst (i.e., inlet and outlet temperatures), along with any other data needed for determination of the NO to $NO_2$ conversion effectiveness of the oxidation catalyst, including but not limited to aging information on the catalyst (e.g., cumulative hours of operation and/or cumulative hours of operation during post injection), exhaust flow rate, and post injection fuel quantity.

From box 108, the logic path proceeds to decision node 112, which compares the ratio of NO and $NO_2$ in the exhaust gas against a predetermined value such as a value needed for desired performance of SCR catalyst 16 (FIG. 1), or a value that may be calculated or determined from a lookup table by the control module 30 or other system-level control microprocessors based on engine, exhaust, or other system parameters such as exhaust temperature, exhaust flow rate, upstream $NO_x$ concentration, and the like. If the ratio of $NO_2$ to NO in the exhaust gas falls outside the target level or range, then control proceeds along path 114 to step 118 where control module 30 (FIG. 1) generates an error alert notification or other appropriate system-level communication signal, followed by a return to box 101 to await or begin the next diagnostic routine. If the ratio of $NO_2$ to NO in the exhaust gas satisfies the target level or range, then control proceeds along path 122 to box 101 to await or begin the next diagnostic routine.

In another exemplary embodiment, decision node 112 can compare the respective levels of NO and $NO_2$ downstream of the oxidation catalyst to the levels upstream of the oxidation catalyst and compare against a targeted value or range. The upstream NO and $NO_2$ levels can be directly measured by a second gas sensor (not shown) upstream of the oxidation catalyst or they can be estimated based on system information such as engine operating parameters.

Gas sensors used in the practice of the invention include a plurality of sensing or pumping cells, wherein a first cell is capable of producing a first output that is indicative of a concentration of $NO_2$ alone or in combination with one or more other constituents, and a second cell is capable of producing a second output that is indicative of a concentration of NO alone or in combination with one or more other constituents. If the first output is indicative of the concentration of $NO_2$ in combination with one or more other constituents, the sensor comprises cells with sensing capabilities sufficient to isolate the contribution of $NO_2$ concentration to the first output. Additionally, if the second output is indicative of the concentration of NO in combination with one or more other constituents, the sensor comprises cells with sensing capabilities sufficient to isolate the contribution of NO concentration to the second output. Such sensors are known to those of ordinary skill in the art and are disclosed, for example, in US patent application publication nos. US 2010/0077833 A1 and/or US 2010/0161242 A1, the disclosures of both of which are incorporated herein by reference in their entirety.

In an exemplary embodiment, the gas sensor comprises a $NO_2$ sensing cell that produces an output that is indicative of $NO_2$ concentration in the exhaust gas and a $NO_x$ pumping cell that produces an output that is indicative of combined concentration of $NO_2$ and NO in the exhaust gas. Such gas sensors are described, for example, in the above-referenced US 2010/0161242 A1. If the engine is capable of producing exhaust gas that contains measurable levels of ammonia under some operating conditions, then the gas sensor can also include a $NH_3$ sensing cell that produces an output that is indicative of $NH_3$ concentration in the exhaust gas. Such an $NH_3$ sensing cell would allow for $NH_3$ content to be subtracted from the reading produced by the $NO_x$ pumping cell, which generally does not distinguish between NO, $NO_2$, and $NH_3$ content in the exhaust gas.

In another exemplary embodiment, the gas sensor comprises a $NO_2$ Nernst cell that produces an output that is indicative of $NO_2$ concentration in the exhaust gas and a $NO_x$ Nernst cell that produces an output that is indicative of combined $NO_2$ and NO concentration in the exhaust gas. Such gas sensors are described, for example, in the above-referenced US 2010/0077833 A1.

While the invention has been described with reference to exemplary embodiments, it will be understood by those skilled in the art that various changes may be made and equivalents may be substituted for elements thereof without departing from the scope of the invention. In addition, many modifications may be made to adapt a particular situation or material to the teachings of the invention without departing from the essential scope thereof. Therefore, it is intended that the invention not be limited to the particular embodiments disclosed, but that the invention will include all embodiments falling within the scope of the present application.

What is claimed is:

1. An engine exhaust treatment system fluidly coupled to an internal combustion engine, comprising:
    an oxidation catalyst disposed in an engine exhaust stream;
    a reductant source for injecting a reductant into the exhaust stream downstream of the oxidation catalyst;
    an SCR catalyst disposed in the exhaust stream downstream of the reductant source; and
    a gas sensor, disposed in the exhaust stream downstream of the oxidation catalyst and upstream of the reductant source, comprising a plurality of sensing or pumping cells, wherein a first cell is capable of producing a first output that is indicative of a concentration of $NO_2$ alone or in combination with one or more other constituents, and a second cell is capable of producing a second output that is indicative of a concentration of NO alone or in combination with one or more other constituents, and further wherein if the first output is indicative of the concentration of $NO_2$ in combination with one or more other constituents, the sensor comprises cells with sensing capabilities sufficient to isolate the contribution of $NO_2$ concentration to said first output, and if the second output is indicative of the concentration of NO in combination with one or more other constituents, the sensor comprises cells with sensing capabilities sufficient to isolate the contribution of NO concentration to said second output.

2. The system of claim 1, further comprising a controller in communication with the gas sensor, the controller configured to determine a conversion of NO to $NO_2$ by the oxidation catalyst.

3. The system of claim 2, wherein the controller is configured to generate an error alert signal if the conversion of NO to $NO_2$ by the oxidation catalyst falls below a predetermined value.

4. The system of claim 2, wherein the controller is configured to generate an error alert signal if the ratio of $NO_2$ to NO downstream of the oxidation catalyst falls below a predetermined value.

5. The system of claim 2, wherein the controller is configured to calculate an estimated ratio of NO to $NO_2$ in the exhaust stream upstream of the oxidation catalyst, and to compare said calculated estimate with NO and $NO_2$ concentrations determined from the gas sensor downstream of the oxidation catalyst to determine an NO to $NO_2$ conversion effectiveness of the oxidation catalyst.

6. The system of claim 1, wherein the gas sensor comprises a $NO_2$ sensing cell that produces an output that is indicative of $NO_2$ concentration in the exhaust gas and a $NO_x$ pumping cell that produces an output that is indicative of combined of $NO_2$ and NO concentration in the exhaust gas.

7. The system of claim 1, wherein the gas sensor comprises a $NO_2$ Nernst cell that produces an output that is indicative of $NO_2$ concentration in the exhaust gas and a $NO_x$ Nernst cell that produces an output that is indicative of combined $NO_2$ and NO concentration in the exhaust gas.

8. The system of claim 1, further comprising a particulate filter located downstream of the SCR catalyst.

9. A method of assessing performance an exhaust treatment system comprising an oxidation catalyst disposed in an engine exhaust stream, a reductant source for injecting a reductant into the exhaust stream downstream of the oxidation catalyst, and an SCR catalyst disposed in the exhaust stream downstream of the reductant source, the method comprising:
    reading the output of a gas sensor, disposed in the exhaust stream downstream of the oxidation catalyst, to determine the concentrations of NO and $NO_2$ in the exhaust stream downstream of the oxidation catalyst, said gas sensor comprising a plurality of sensing or pumping cells, wherein a first cell is capable of producing a first output that is indicative of a concentration of $NO_2$ alone or in combination with one or more other constituents, and a second cell is capable of producing a second output that is indicative of a concentration of NO alone or in combination with one or more other constituents, and further wherein if the first output is indicative of the concentration of $NO_2$ in combination with one or more other constituents, the sensor comprises cells with sensing capabilities sufficient to isolate the contribution of $NO_2$ concentration to said first output, and if the second output is indicative of the concentration of NO in combination with one or more other constituents, the sensor comprises cells with sensing capabilities sufficient to isolate the contribution of NO concentration to said second output; and
    generating an alert signal if either or both of the concentrations of NO and $NO_2$ or the ratio of NO content to $NO_2$ content in the exhaust stream downstream of the oxidation catalyst fall outside a target level or range.

10. The method of claim 9, wherein the target level or range is a predetermined value.

11. The method of claim 9, wherein the alert signal is generated if the $NO_2$ content or the ratio of $NO_2$ to NO content in the exhaust gas exceeds a predetermined value.

12. The method of claim 9, wherein the target level or range is calculated based on concentration of NO and $NO_2$ in the exhaust stream upstream of the oxidation catalyst and a target conversion of NO to $NO_2$ by the oxidation catalyst.

13. The method of claim 12, wherein the concentration of NO and $NO_2$ in the exhaust stream upstream of the oxidation is calculated based on one or more of engine operating parameters, exhaust treatment system operating parameters, or environmental parameters.

14. The method of claim 9, wherein the gas sensor comprises a $NO_2$ sensing cell that produces an output that is indicative of $NO_2$ concentration in the exhaust gas and a $NO_x$ pumping cell that produces an output that is indicative of combined of $NO_2$ and NO concentration in the exhaust gas.

15. The method of claim 9, wherein the gas sensor comprises a $NO_2$ Nernst cell that produces an output that is indicative of $NO_2$ concentration in the exhaust gas and a $NO_x$ Nernst cell that produces an output that is indicative of combined $NO_2$ and NO concentration in the exhaust gas.

* * * * *